(12) United States Patent
Meyer, Jr. et al.

(10) Patent No.: US 6,312,925 B1
(45) Date of Patent: Nov. 6, 2001

(54) METHODS AND COMPOSITIONS TO FACILITATE D-LOOP FORMATION BY OLIGONUCLEOTIDES

(75) Inventors: Rich B. Meyer, Jr., Bothell, WA (US); Howard B. Gamper, Jr., Philadelphia, PA (US)

(73) Assignee: Epoch Pharmaceuticals, Inc., Bothell, WA (US)

( * ) Notice: Subject to any disclaimer, the term of this patent is extended or adjusted under 35 U.S.C. 154(b) by 0 days.

(21) Appl. No.: 09/074,626

(22) Filed: May 7, 1998

Related U.S. Application Data

(60) Provisional application No. 60/045,936, filed on May 8, 1997.

(51) Int. Cl.⁷ .................................................. C12P 19/34
(52) U.S. Cl. .......................................... 435/91.1; 435/91.4
(58) Field of Search ................................ 435/91.1, 91.4, 435/91.51

(56) References Cited

U.S. PATENT DOCUMENTS

| | | | |
|---|---|---|---|
| 4,835,263 | 5/1989 | Nguyen et al. | 536/24.3 |
| 5,149,966 | 9/1992 | Silari et al. | 428/406 |
| 5,273,881 | 12/1993 | Sena et al. | 435/6 |
| 5,422,251 | 6/1995 | Fresco | 435/91.1 |
| 5,574,142 | 11/1996 | Meyer, Jr. et al. | 536/23.1 |
| 5,594,121 | 1/1997 | Froehler et al. | 536/23.5 |
| 5,602,240 | 2/1997 | De Mesmaeker et al. | 536/22.1 |

FOREIGN PATENT DOCUMENTS

| | | |
|---|---|---|
| 90/03370 | 4/1990 | (WO) . |
| 90/06934 | 6/1990 | (WO) . |
| 93/03736 | 3/1993 | (WO) . |
| 93/10820 | 6/1993 | (WO) . |
| 94/13325 | 6/1994 | (WO) . |
| 94/17092 | 8/1994 | (WO) . |
| 96/32496 | 10/1996 | (WO) . |
| 96/40711 | 12/1996 | (WO) . |
| 97/12896 | 4/1997 | (WO) . |

OTHER PUBLICATIONS

Gamper, H. B. et al., "Strand invasion of supercoiled DNA by oligonucleotides with a triplex guide sequence." *J. Am. Chem. Soc.* 120(9):2182–2183 (1998).
Asseline et al,. (1984) "Nucleic acid–binding molecules with high affinity and base sequence specificity: Intercalating agents covalently limked to oligodeoxynucleotides" *Proc. Natl. Acad. Sci. USA* 81:3297–3301.
Benimetskaya et al,. (1989) "Site—specific laser modification (cleavage) of oligodeoxynucleotides" *Biopolymers* 28:1129–1147.
Bolli et al., (1996) "Watson–Crick base–pairing properties of bicyclo–DNA" *Nucl. Acids Res.* 24:4660–4667.
Corey et al. (1995) "Strand invasion by oligonucleotide–nuclease conjugates" *Bioconjug. Chem.* 6:93–100.
Demidov et al., (1995) "Kinetics and mechanism of polyamide( "peptide") nucleic acid binding to duplex DNA" *Proc. Natl. Acad. Sci. USA* 92:2637–2641.
Escudé et al., (1995) "Selective stabilization of DNA triple helices by benzopyridoindole derivatives" *J. Am. Chem. Soc.* 117:10212–10219.
Gryaznov et al., (1992) "Synthesis and properties of oligonucleotides containing aminodeoxythymidine units" *Nucleic Acids Res.* 20:3403–3409.
Gryaznov et al., (1994) "Oligodeoxyribonucleotide N3'→P5' phosphoramidates: Synthesis and hybridization properties" *J. Am. Chem. Soc.* 116:3143–3144.
Iyer et al., (1995) "Accelerated hybridization of oligonucleotides to duplex DNA" *Biol Chem.* 270:14712–14717.
Kazimierczuk et al., (1984) "Synthesis of 2' –deoxytubercidin, 2' –deoxyadenosine, and related 2' –deoxynucleosides via a novel direct stereospecific sodium salt glycosylation procedure" *J. Am. Chem. Soc.* 106:6379–6382.
Kutyavin et al., (1996) "Oligonucleotids containing 2–Aminoadenine and 3–Thiothymine act as selectively binding complementary agents" Biochemistry 35:11170–11176.
Lee et al., (1993) "Coralyne binds tightly to both T–A–T–and C–G–C–⁺ containing DNA triplexes" *Biochemistry* 32:5591–5597.
Letsinger, R.L. and Schott, M.E., (1981) "Selectivity in binding a phenanthridiniumdinucleotide derivative to homopolynucleotides" *J. Am. Chem. Soc.* 103:7394–7396.
Lokhov et al., (1992) "Synthesis and high stability of complementary complexes of N–(2–hydroxyethyl)phenazinium dervatives of oligonucleotides" *Bioconjugate Chem.* 3:413–419.
Lukhtanov et al., (1995) "Oligodeoxyribonucleotides with conjugated dihydropyrroloindole oligopeptides: Preparation and hybridization properties" *Bioconjugate Chemistry* 6:418–426.
Lukhtanov et al., (1996) "Rapid and efficient hybridization–triggered crosslinking within a DNA duplex by an oligodeoxyribonucleotide bearing a conjugated cyclopropapyrroloindole" *Nucleic Acids Res.* 24:683–687.

(List continued on next page.)

Primary Examiner—James Martinell
(74) Attorney, Agent, or Firm—Townsend and Townsend and Crew LLP

(57) ABSTRACT

Methods and compositions for efficient targeting and modification of target sequences in duplex DNA are provided, utilizing oligonucleotides or oligonucleotide compositions containing two domains. The first domain comprises an entity capable of recognizing a double-stranded DNA sequence. This can be a protein, peptide, antibiotic, minor groove binding agent or a nucleotide sequence capable of triplex formation The second domain, which is covalently joined to the first, is capable of recognizing a single-stranded DNA sequence. This second domain will most often be complementary, in the Watson-Crick sense, to a target sequence in the double-stranded nucleic acid. The second domain can optionally carry one or more modifying groups, capable of causing a mutation, a pre-mutagenic lesion, or some other type of heritable change in the target sequence.

24 Claims, 4 Drawing Sheets

OTHER PUBLICATIONS

Marchand et al., (1996) "Stabilization of triple helical DNA by a benzopyridoquinoxaline intercalator" *Biochemistry* 35:5022–5032.

Mouscadet et al., (1994) "Triple helix formation with short oligonucleotide–intercalator conjugates matching the HIV–1 U3 LTR end sequence" *Biochemistry* 33:4187–4196.

Nielsen et al., (1991) "Sequence–selective recognition of DNA by strand displacement with a thymine–substituted polyamide" *Science* 254:1497–1500.

Reed et al., (1995) "Synthesis and evaluation of nuclear targeting peptide–antisense oligodeoxynucleotide conjugates" *Bioconjugate Chem.* 6:101–108.

Robles et al., (1996) "A parallel–stranded DNA triplex tethering a Hoechst 33258 analogue results in complex stabilization by simultaneous major groove and minor groove binding" *J. Am. Chem. Soc.* 118:5820–5821.

Sinyakov et al., (1995) "Exceptional and selective stabilization of A–T rich DNA–DNA duplexes by N–methylpyrrole carboxamide peptide conjugated to oligodexynucleotides" *J. Am. Chem. Soc.* 117:4995–4996.

Sun, J–S. and Hélène, C., (1993) "Oligonucleotide–directed triple–helix formation" *Curr. Opin. Struct. Biol.* 3:345–356.

Sun et al., (1996) "Oligonucleotide–direct triple–helix formation" *Curr. Opin. Struct. Biol.* 6:327–333.

Sun et al., (1987) "Oligo–[a]–deoxynucleotides covalently limked to an intercalating agent" *Nucl. Acids Res.* 15:6149–6158.

Szewczyk et al., (1996) "Cooperative triple–helix formation via a minor groove dimerization domain" *J. Am. Chem. Soc.* 118:6778–6779.

Webb, T.R. and Matteucci, M.D., (1986) "Sequence–specific cross–linking of deoxyoligonicleotides via hybridization–triggered alkylation" *J. Am. Chem. Soc.* 108:2764–2765.

Webb, T.R. and Matteucci, M.D., (1986) "Hybridization triggered cross–linking of deoxyoligonucleotides" *Nucleic Acids Res.* 14:7661–7674.

Wilson et al., (1993) "DNA triple–helix specific intercalators as antigene enhancers: Unfused aromatic cations" *Biochemistry* 32:10614–10621.

Zhou et al., (1995) "Stable triple helices formed by acridine–containing oligonucleotides with oligopurine tracts of DNA interrupted by one or two pyrimidines" *J. Am. Chem. Soc.* 117:10425–10428.

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

ACGCTGAATT CTGCATGCTA TCCCCTTTTC TCTCCTTTCT ATCAGCTGCA GATCCTTAGC    60

(2) INFORMATION FOR SEQ ID NO: 2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

GCTAAGGATC TGCAGCTGAT AGAAAGGAGA GAAAAGGGGA TAGCATGCAG AATTCAGCGT      60

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 2
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 6..7
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 9
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 11
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 16..19
        (D) OTHER INFORMATION: /mod_base= OTHER
            /note= "N = 5-methyl-2'-deoxycytidine"

(xi) SEQUENCE DESCRIPTION: SEQ ID NO: 3:

TNTTTNNTNT NTTTTNNNNT      20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

TAGCATGCAG AATTCAGCGT      20

(2) INFORMATION FOR SEQ ID NO: 5:

```
        (i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 2
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 6..7
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 9
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 11
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 16..19
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 26
            (D) OTHER INFORMATION: /mod_base= OTHER
                /note= "N =
                5-(3-aminopropyl-2'-deoxyuridine"

(xi) SEQUENCE DESCRIPTION: SEQ ID NO: 5:

TNTTTNNTNT NTTTTNNNNT TAGCANGCAG AATTCAGCGT                           40

(2) INFORMATION FOR SEQ ID NO: 6:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 2
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 6..7
            (D) OTHER INFORMATION: /mod_base= OTHER
                /note= "N = 5-methyl-2'-deoxycytidine"

(ix) FEATURE:
            (A) NAME/KEY: modified_base
            (B) LOCATION: 9
            (D) OTHER INFORMATION: /mod_base= OTHER
                /note= "N = 5-methyl-2'-deoxycytidine"

(ix) FEATURE:
```

(A) NAME/KEY: modified_base
        (B) LOCATION: 11
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 16..19
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 26
        (D) OTHER INFORMATION: /mod_base= OTHER
            /note= "N =
            5-(3-bromoacetamidopropyl-2'-
            deoxyuridine"

(xi) SEQUENCE DESCRIPTION: SEQ ID NO: 6:

TNTTTNNTNT NTTTTNNNNT TAGCANGCAG AATTCAGCGT                              40

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

GCTAAGGATC TGCAGCTGAT                                                   20

(2) INFORMATION FOR SEQ ID NO: 8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 11
        (D) OTHER INFORMATION: /mod_base= OTHER
            /note= "N =
            5-(3-aminopropyl-2'-deoxyuridine"

(ix) FEATURE:
        (A) NAME/KEY: modified_base
        (B) LOCATION: 22
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 26..27
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 29
        (D) OTHER INFORMATION: /mod_base= OTHER
            /note= "N = 5-methyl-2'-deoxycytidine"

(ix) FEATURE:
        (A) NAME/KEY: modified_base
        (B) LOCATION: 31
        (D) OTHER INFORMATION: /mod_base= OTHER
            /note= "N = 5-methyl-2'-deoxycytidine"

```
    (ix) FEATURE:
          (A) NAME/KEY: modified_base
          (B) LOCATION: 36..39
          (D) OTHER INFORMATION: /mod_base= OTHER
              /note= "N = 5-methyl-2'-deoxycytidine"

(xi) SEQUENCE DESCRIPTION: SEQ ID NO: 8:

GCTAAGGATC NGCAGCTGAT TNTTTNNTNT NTTTTNNNNT                                       40

(2) INFORMATION FOR SEQ ID NO: 9:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: modified_base
          (B) LOCATION: 11
          (D) OTHER INFORMATION: /mod_base= OTHER
              /note= "N =
              5-(3-bromoacetamidopropyl-2'-
              deoxyuridine"

(ix) FEATURE:
          (A) NAME/KEY: modified_base
          (B) LOCATION: 22
          (D) OTHER INFORMATION: /mod_base= OTHER
              /note= "N = 5-methyl-2'-deoxycytidine"

(ix) FEATURE:
          (A) NAME/KEY: modified_base
          (B) LOCATION: 26..27
          (D) OTHER INFORMATION: /mod_base= OTHER
              /note= "N = 5-methyl-2'-deoxycytidine"

(ix) FEATURE:
          (A) NAME/KEY: modified_base
          (B) LOCATION: 29
          (D) OTHER INFORMATION: /mod_base= OTHER
              /note= "N = 5-methyl-2'-deoxycytidine"

(ix) FEATURE:
          (A) NAME/KEY: modified_base
          (B) LOCATION: 31
          (D) OTHER INFORMATION: /mod_base= OTHER
              /note= "N = 5-methyl-2'-deoxycytidine"

(ix) FEATURE:
          (A) NAME/KEY: modified_base
          (B) LOCATION: 36..39
          (D) OTHER INFORMATION: /mod_base= OTHER
              /note= "N = 5-methyl-2'-deoxycytidine"

(xi) SEQUENCE DESCRIPTION: SEQ ID NO: 9:

GCTAAGGATC NGCAGCTGAT TNTTTNNTNT NTTTTNNNNT                                       40

(2) INFORMATION FOR SEQ ID NO: 10:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 10:

CCCTGGCGCC GCTTCTTTGA G                                                           21
```

METHODS AND COMPOSITIONS TO FACILITATE D-LOOP FORMATION BY OLIGONUCLEOTIDES

CROSS-REFERENCE TO RELATED APPLICATIONS

This application claims priority to U.S. Provisional Patent Application No. 60/045,936, filed on May 8, 1997.

STATEMENT OF RIGHTS TO INVENTIONS MADE UNDER FEDERALLY SPONSORED RESEARCH

Not applicable.

TECHNICAL FIELD

The invention is in the field of genetic modification. More particularly, it is in the field of modified oligonucleotides for use in gene targeting, gene modification and genetic therapy.

BACKGROUND

Targeted modification of a chromosomal gene in a living cell is central to the development of gene therapy. To be maximally effective, such targeted modification results in the change of one or more nucleotides in the sequence of a chromosomal gene. Specific examples include conversion of a mutant allele into its wild-type counterpart and inactivation of a deleterious gene by creating a nucleotide sequence specifying premature transcriptional or translational termination, or altered RNA processing.

A serious challenge to the development of effective compositions and methods for targeted modification has been the difficulty in designing modifying agents which are capable of stable interaction with a target sequence, but retain the specificity necessary for targeted modification. For example, certain intercalating agents have a high affinity for DNA, but react non-specifically with numerous different DNA sequences. On the other hand, reagents that are highly specific for a particular nucleotide sequence, such as complementary oligonucleotides, often do not have sufficient affinity for a target sequence to allow efficient targeted modification to proceed on a reasonable time scale.

Several approaches to sequence-specific modification of a target double-stranded nucleotide sequence have been attempted. The use of triplex-forming oligonucleotides with attached modifying groups has been described in WO 94/17092 and WO 96/40711. These reagents are capable of recognizing a target sequence comprising base-paired, double-stranded DNA, and forming a triple-stranded structure that is mediated by a type of base-pairing different than Watson-Crick type base-pairing. Fresco, U.S. Pat. No. 5,422,251. Attachment of a suitable chemical modifying agent to such an oligonucleotide makes it possible to generate a lesion at or near a target sequence in a gene of interest. Subsequent cellular processes related to DNA replication, recombination and/or repair can result in either restoration of the original sequence by repair of the lesion, or mutagenesis, for example by misrepair, resulting in a base change at the site of the lesion. However, formation of triplexes that are sufficiently stable to achieve modification of a target sequence require sequences containing at least about 12 consecutive purine residues on one strand. Consequently, targeting strategies utilizing modified triplex-forming oligonucleotides are restricted to genes having the requisite homopurine runs.

An alternative approach to targeted modification involves the use of modified oligonucleotides having traditional Watson-Crick complementarity to a target sequence, in concert with a recombinase enzyme. The recombinase enzyme facilitates strand invasion at the target sequence by the complementary oligonucleotide, with the formation of a D-loop-type structure. See WO 93/03736 and WO 96/40711. Efficient formation of this structure and hence, efficient modification, requires at least approximately 26 nucleotides of homology between the oligonucleotide and its target sequence, as described in WO 96/40711. In addition, the method depends on either deliberate or fortuitous interaction between the oligonucleotide and a recombinase enzyme, which may be difficult to control.

Thus, a facile method for non-enzymatic targeting of specific sequences in double-stranded DNA that is more broadly applicable than conventional triplex targeting, along with compositions for use in such a method, would greatly enhance the field of gene therapy. Methods and compositions designed to facilitate the interaction of a complementary oligonucleotide with a target sequence have heretofore relied on attaching the oligonucleotide to an agent having non-specific affinity for DNA, such as an intercalating agent, staphylococcal nuclease or short synthetic positively-charged peptides. U.S. Pat. No. 4,835,263; Mouscadet et al. (1994) *Biochemistry* 33:4187–4196; Corey et al. (1995) *Bioconjug. Chem.* 6:93–100; and Iyer et al. (1995) *J. Biol. Chem.* 270:14712–14717. However, these agents possess only a weak general affinity for DNA and thus are not able to localize the oligonucleotide to the vicinity of its target sequence.

Displacement loop (D-loop) formation offers, in principle, no limits on targeting sequence but faces significant thermodynamic and topological issues. Peptide nucleic acids can form D-loop like structures by strand invasion, but only at homopurine runs. The versatility of Watson-Crick sequence targeting might be realized if: (a) D-loop formation could be facilitated and (b) the unstable D-loop could be stabilized.

DISCLOSURE OF THE INVENTION

The present invention provides new methods and compositions for the targeting and/or modification of a specific sequence in a double-stranded DNA molecule, thereby increasing the number and variety of such sequences that are amenable to targeting and/or modification by a complementary oligonucleotide. Recognition of the target sequence occurs with high affinity and with a high degree of selectivity as a result of two types of sequence specificity, which are provided by an oligonucleotide or oligonucleotide composition comprising two functional domains.

The first functional domain comprises an entity capable of recognizing a double-stranded DNA sequence. This can be a protein, peptide, antibiotic, minor groove binding agent or a nucleotide sequence capable of triplex formation. The first domain may also optionally carry one or more modifying groups. The second functional domain, which is covalently joined to the first, is capable of recognizing a single-stranded DNA sequence. This second domain will most often be substantially complementary, in the Watson-Crick sense, to a target sequence in a double-stranded nucleic acid. The second functional domain can optionally carry one or more modifying groups, capable of causing a mutation, a pre-mutagenic lesion, or some other type of heritable change in the target sequence. Either of the two domains can also include moieties which facilitate their sequence-specific interaction with a double-stranded DNA molecule.

By providing a non-enzymatic targeting method that does not rely exclusively upon triplex homology, the practice of the present invention significantly broadens the repertoire of sequences in double-stranded DNA which can be targeted and/or modified. In the practice of the invention, D-loop formation is facilitated by the first domain, which tethers the D-loop-forming domain to the vicinity of the target sequence. Furthermore, potentially unstable D-loops, once formed, can be stabilized through the action of reactive groups attached to the D-loop-forming domain.

In one embodiment, the present invention provides oligonucleotides and oligonucleotide compositions comprising a triplex-forming domain and a D-loop-forming domain, wherein the former is capable of facilitating strand invasion by the latter. Optionally, a reactive group in the D-loop-forming domain can permanently stabilize that structure, once formed.

In another embodiment, the present invention provides a method for modifying a target nucleotide sequence in a double-stranded DNA molecule, by contacting the double-stranded DNA molecule with an oligonucleotide composition containing a first functional domain and a second functional domain wherein the first functional domain recognizes a region of double-stranded DNA adjacent to or in the vicinity of the target sequence, the second functional domain is substantially complementary, in the Watson-Crick sense, to the target nucleotide sequence and wherein the second functional domain carries an attached modifying agent capable of modifying the target nucleotide sequence.

In another embodiment, the present invention provides a method for modifying a target nucleotide sequence in a double-stranded DNA molecule by contacting the double-stranded DNA molecule with an oligonucleotide containing a first functional domain and a second functional domain wherein the first functional domain binds to a site adjacent to or in the vicinity of the target sequence by triplex formation, the second functional domain is substantially complementary, in the Watson-Crick sense, to the target nucleotide sequence and wherein the second functional domain carries an attached modifying agent capable of modifying the target nucleotide sequence.

The invention additionally provides a method for targeting a nucleotide sequence in a double-stranded DNA molecule by contacting the double-stranded DNA molecule with an oligonucleotide composition comprising a first functional domain and a second functional domain wherein the first functional domain recognizes a double-stranded DNA sequence adjacent to or in the vicinity of the target sequence and the second functional domain is substantially complementary, in the Watson-Crick sense, to the target nucleotide sequence.

In addition, the present invention provides a method for targeting a nucleotide sequence in a double-stranded DNA molecule by contacting the double-stranded DNA molecule with an oligonucleotide comprising a first functional domain and a second functional domain wherein the first functional domain binds to a site adjacent to or in the vicinity of the target sequence by triplex formation and the second functional domain is substantially complementary, in the Watson-Crick sense, to the target nucleotide sequence.

In another embodiment, the invention provides an oligonucleotide or oligonucleotide composition (such as an oligonucleotide conjugate) for targeting and/or modifying a target sequence in a double-stranded DNA molecule, wherein the oligonucleotide or oligonucleotide composition comprises a first functional domain and a second functional domain wherein the first functional domain recognizes a double-stranded DNA sequence adjacent to or in the vicinity of the target sequence, the second functional domain is substantially complementary, in the Watson-Crick sense, to the target nucleotide sequence, and wherein the second functional domain optionally carries an attached modifying agent capable of modifying the target nucleotide sequence.

In another embodiment, the present invention provides an oligonucleotide or oligonucleotide composition (such as an oligonucleotide conjugate) for targeting and/or modifying a target nucleotide sequence in a double-stranded DNA molecule, wherein the oligonucieotide comprises a first functional domain and a second functional domain wherein the first functional domain binds to a site adjacent to or in the vicinity of the target sequence by triplex formation, the second functional domain is complementary, in the Watson-Crick sense, to the target nucleotide sequence and wherein the second functional domain optionally carries an attached modifying agent capable of modifying the target nucleotide sequence.

The methods of the invention can be performed in vitro or in vivo, and the target sequence can be present in the genome of a plant, animal, bacterium, virus or other DNA-containing organism.

The methods and compositions of the invention can be used for gene mapping, gene therapy and other techniques that require sequence-specific recognition of a target nucleotide sequence in a double-stranded nucleic acid. The present invention expands the range of double-stranded DNA sequences capable of being targeted and/or modified by making possible the temporary localization of the targeting or modifying moiety in the vicinity of the target sequence. By the use of appropriate modifying groups attached to the second functional domain, it is possible to generate sequence changes in the target sequence, which can result either in a mutation or in reversion of a mutation to the wild-type sequence.

All patents and publications mentioned herein, either supra or infra, are hereby incorporated by reference in their entirety.

BRIEF DESCRIPTION OF THE DRAWINGS

FIG. 2A shows an ethidium bromide-stained gel;

FIGS. 2B and 2C show detection of labeled oligonucleotide by autoradiography of dried gels.

MODES FOR CARRYING OUT THE INVENTION

Figure 1:
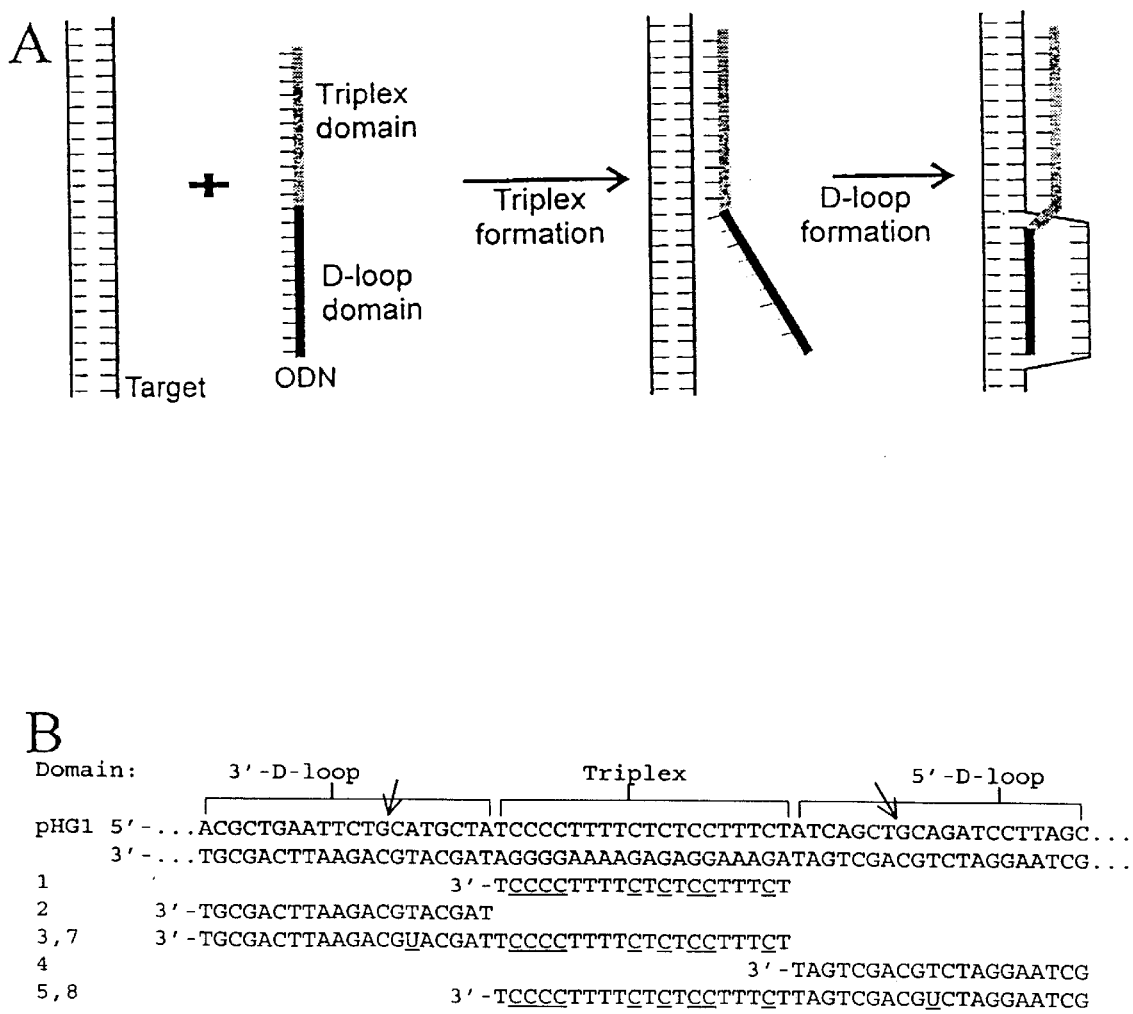
FIG. 1A shows a schematic diagram of triplex formation, followed by D-loop formation, between an oligonucleotide composition of the invention and a double-stranded DNA target.
FIG. 1B shows a partial sequence of the plasmid pHG1 (top two lines, (SEQ ID NOS: 1 and 2), and the sequences of various oligonucleotides used to target or to modify that sequence. Triplex-forming and D-loop-forming regions of the pHG1 sequence are indicated. In this figure, C represents 5-methyl-2'-deoxycytidine; U represents 5-(3-aminopropyl)-2'-deoxyuridine in oligonucleotides 3 (SEQ ID NO: 5) and 5 (SEQ ID NO: 8), and U represents 5-(3-bromoacetamidopropyl)-2'-deoxyuridine in oligonucleotides 7 (SEQ ID NO: 6) and 8 (SEQ ID NO: 9). Arrows denote the guanine bases in the plasmid alkylated by oligonucleotides 7 (SEQ ID NO: 6) and 8 (SEQ ID NO: 9).

Through the practice of the present invention, the range of double-stranded DNA sequences amenable to sequence-specific targeting and modification is expanded by the use of novel compositions and methods employing these compositions. The methods and compositions of the invention exploit double-strand sequence recognition by a first domain of an oligonucleotide or oligonucleotide composition to facilitate single-strand sequence recognition by a second domain.

The invention will be described with reference to the following terms.

Base-pairing describes an interaction between two nucleotide residues of an oligo- or polynucleotide wherein the two residues are noncovalently linked by hydrogen bonds. Watson-Crick base-pairing is the type which normally occurs in duplex DNA wherein adenine base-pairs with thymine (or uracil) and guanine base-pairs with cytosine. There are also several modes of triplex pairing, wherein a polypurine stretch in one strand of a duplex nucleic acid (which is base-paired to its complementary polypyrimidine strand by Watson-Crick base-pairing) is capable of forming an additional set of hydrogen bonds with a third strand. See the definition of "triplex formation" below.

Complementary or complementarity refers to the ability of nucleotides comprising two oligo- or polynucleotides to base-pair with each other according to the rules of Watson-Crick base-pairing, in which adenine base-pairs with thymine (or uracil) and guanine base-pairs with cytosine. Complementarity includes complete complementarity, in which all nucleotides in a contiguous sequence form complementary base pairs, and substantial complementarity, in which not all nucleotides in a sequence form complementary base pairs, but enough base pairs are formed to maintain a stable duplex structure under the conditions of interaction between the oligo- or polynucleotides.

A D-loop is a structure formed when a short, single-stranded oligo- or polynucleotide, complementary to a portion of a longer double-stranded polynucleotide, invades the double-stranded molecule and base-pairs with its complementary sequence. Under these conditions, one of the strands of the longer molecule is displaced and forms a single-stranded "bubble."

A domain, as used herein, refers to a distinct portion of an oligonucleotide or oligonucleotide composition, which participates in locating and/or modifying the target nucleotide sequence. The compositions of the invention include first and second domains. Without being bound by any particular theory regarding mechanism of action, the first domain aids in localizing the oligonucleotide or oligonucleotide composition to the vicinity of the target nucleotide sequence. The second functional domain interacts directly with the target nucleotide sequence by base-pairing, and can optionally modify the target nucleotide sequence.

An electrophilic group is a reagent or moiety that accepts an electron pair (from a nucleophilic group) to form a covalent bond. In the practice of the invention, electrophilic groups include, but are not limited to, a carbon, phosphorus or sulfur atom which bears an attached leaving group such as, for example, a halogen atom.

The term modify is used herein to refer to a chemical change in the structure of a particular nucleotide sequence. Such changes, or modifications, include, but are not limited to, covalent attachment of an oligonucleotide or functional group, insertion or deletion of one or more nucleotides, change in nucleotide sequence, or inversion of a region of nucleotide sequence.

A modifying agent is any chemical, biological or physical entity capable of causing a modification, as defined above, in a nucleotide sequence.

A mutagen is any chemical, biological or physical entity capable of causing a mutation in a nucleotide sequence. Mutations include, but are not limited to, sequence changes, insertions, deletions, or inversions of a nucleotide sequence.

A nitrogen mustard (or N-mustard) is a moiety comprising one or more leaving groups (typically chloride or fluoride), each attached by a short (preferably, two-carbon) chain to a basic nitrogen atom. A bifunctional nitrogen mustard is a nitrogen mustard comprising two basic nitrogen-leaving group moieties.

An oligonucleotide is a nucleic acid polymer comprising a plurality of nucleotide subunits of defined base sequence. Generally, an oligonucleotide is shorter than 3000 nucleotides in length, preferably, shorter that 150 nucleotides, more preferably shorter than 75 nucleotides and, most preferably, 50 nucleotides or shorter. Oligonucleotides comprise a chain of nucleotides which are linked to one another by phosphate ester linkages. Each nucleotide typically comprises a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose as the sugar moiety. Modified bases and base analogues, modified sugars and sugar analogues and/or phosphate analogues and modified phosphate moieties, known in the art, are also suitable for use in the oligonucleotides of the present invention. As used herein, oligonucleotide also includes polynucleotides.

An oligonucleotide composition refers to a composition comprising an oligonucleotide attached to some other chemical or biological moiety. Suitable examples include, but are not limited to, an oligonucleotide conjugate, in which an oligonucleotide is covalently attached to a protein, peptide, antibiotic, minor groove binder, or intercalating agent. If the other chemical or biological moiety is itself an oligonucleotide sequence, the oligonucleotide composition can comprise an oligonucleotide.

A target nucleotide sequence is a nucleotide sequence in a polynucleotide of interest, which is to be located or modified using the methods of this invention.

Triplex formation refers to the ability of a single-stranded oligonucleotide to bind to a double-stranded oligonucleotide to form a stable three-stranded structure in which each of the three strands interacts with one or more other strands by hydrogen bonding between the heterocyclie bases. The hydrogen bonding between the single-stranded oligonucleotide and one of the strands of the duplex can, for example, be mediated by Hoogsteen base-pairing, reverse Hoogsteen base-pairing or an equivalent type of base-pairing. In the C,T triplex motif, an oligonucleotide containing $N^3$-protonated C residues ($C^+$) and/or T residues is able to form a triplex with a polypurine stretch, in which the third strand is aligned parallel to the polypurine-containing strand and the triplex is stabilized by Hoogsteen base-pairing between $C^+$ and G and between T and A. In the G,A triplex motif, an oligonucleotide containing G residues and/or A residues is able to form a triplex with a polypurine stretch, in which the third strand is aligned antiparallel to the polypurine-containing strand and the triplex is stabilized by reverse Hoogsteen base-pairing between G and G and between A and A. In the G,T triplex motif, an oligonucleotide containing G residues and/or T residues is able to form a triplex with a polypurine stretch, in which the third strand may be aligned either parallel or antiparallel to the polypurine-containing strand and the triplex may be stabilized by either Hoogsteen or reverse Hoogsteen base-pairing between G and G and between T and A. Modified bases or base analogues, for example 8-oxo-adenosine, pseudoisocytidine, 5-methyl cytidine, inosine, 2-aminopurine and various pyrrolo- and pyrazolopyrimidine derivatives, may also be included in a third strand, as they are able to form Hoogsteen and reverse Hoogsteen base pairs with the naturally-occurring bases. Similarly, modified sugar residues or analogues, for example 2'-O-methylribose or peptide nucleic acid backbones, can also form part of a third strand. See, for example, Sun and Hélène (1993) Curr. Opin. Struct. Biol. 3:345–356.

A triplex stabilizer is a molecule that interacts specifically with triple-stranded nucleic acid structures by stacking between the base triads in a triplex, thereby enhancing the stability of the triplex.

The practice of the present invention will employ, unless otherwise indicated, conventional techniques in organic chemistry, biochemistry, oligonucleotide synthesis and modification, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, el al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

Compositions

Oligonucleotides or oligonucleotide compositions comprising two domains have now been found to be useful for targeting and for sequence-specific modification of single-stranded target sequences in double-stranded DNA molecules, in that they provide an improved two-step mechanism for the recognition of target sequences, thereby expanding the range of double-stranded sequences capable of being targeted and/or modified. Previous methods have depended upon either recognition of a double-stranded sequence by triplex formation, or assisted recognition of a single-stranded target in double-stranded DNA by forming a nucleoprotein filament between a recombinase and a single-stranded oligonucleotide. Recognition by triplex formation is limited by the requirement that the target sequence include a polypurine stretch, while single-strand recognition has been limited by the requirement for an associated recombinase. The present invention provides, for the first time, compositions and methods allowing single-strand recognition without the requirement for a recombinase. Temporary localization of a second domain (containing a duplex-forming region) by a first domain (capable of recognizing and interacting with a double-stranded sequence) provides an increased probability of interaction between the second domain and a target sequence. As a result, the range of potential target sequences is considerably expanded, compared to previous targeting methods.

An oligonucleotide composition refers to a composition comprising an oligonucleotide attached to some other chemical or biological moiety, for example, a protein, peptide, antibiotic, minor groove binder, or intercalating agent. For convenience, the terms "oligonucleotide" and "oligonucleotide composition" are used interchangeably herein.

Target binding by an oligonucleotide complementary to a single-stranded target sequence in a double-stranded DNA molecule requires that the DNA molecule comprising the target sequence become at least partially denatured in the region encompassing the target sequence. Although denaturation of a target nucleic acid is easily accomplished in vitro, conditions promoting denaturation, such as high temperature or high concentrations of organic solvents, are often incompatible with cell viability. Consequently, recognition of target DNA sequences in living cells has heretofore relied upon the tendency of DNA to undergo transient local denaturation, also known as DNA "breathing." However, since DNA breathing is a transient phenomenon, the likelihood of an oligonucleotide being in the vicinity of its target sequence at the exact moment that that target sequence "breathes" is extremely small.

The oligonucleotides and oligonucleotide compositions of the present invention comprise a first domain that can tether a complementary oligonucleotide in the vicinity of its target sequence in a double-stranded DNA molecule. The first domain can achieve this function through a sequence-specific interaction with a double-stranded DNA sequence. Thus, the second domain becomes localized near its target sequence so that, when the target sequence undergoes breathing, strand invasion by the second domain occurs, followed by D-loop formation between the second domain and its target sequence. This oligonucleotide-target interaction can be made permanent by the action of a modifying group that is optionally attached to the oligonucleotide sequence comprising the second domain.

In a preferred embodiment, the first domain is a nucleotide sequence capable of triplex formation with a specific homopurine/homopyrimidine run in a double-stranded DNA molecule. The second domain comprises a nucleotide sequence having Watson-Crick complementarity to one of the two strands of the target sequence such that, in a preferred embodiment, it is able to form a D-loop with the target sequence immediately adjacent to the triplex formed by the first domain. Such a complementary oligonucleotide sequence, by itself, would have a low probability of locating its target sequence on a large, chromosome-sized DNA molecule and, having located the target sequence, also would have a low probability of invading the double-stranded structure to form a D-loop with the target sequence.

In the present invention, the first domain can tether the complementary sequence of the second domain to a double-stranded nucleic acid at a site adjacent to the target sequence. This increases the local concentration of the second domain in the vicinity of the target site, making it more likely that the second domain invades the duplex in the region of the target sequence to form a D-loop structure. A D-loop is a structure in which a short, single-stranded nucleic acid invades a longer duplex nucleic acid to form a region in which the short nucleic acid is base-paired with one of the longer strands of the original duplex, and the other longer strand of the duplex constitutes a displaced single strand in the region of complementarity between the short nucleic acid and the duplex.

The second domain of the oligonucleotide, which is complementary to the target nucleotide sequence, is brought into the vicinity of the target sequence by virtue of specific interaction between the first domain and a region of the polynucleotide adjacent to the target sequence. Once they have been brought into proximity, interaction of the second domain with the target sequence, by Watson-Crick base pairing, takes advantage of the tendency for DNA to undergo transient local denaturation, also known as "breathing." The probability of a given stretch of double-stranded DNA undergoing breathing is directly related to its adenine+thymine content, and is enhanced by superhelical stress. The likelihood that a single-stranded oligonucleotide complementary to a short region of a long double-stranded DNA molecule would encounter its target sequence at the same moment that the target sequence were transiently unpaired is very small. However, being tethered in the vicinity of a target sequence (by a first domain) increases the probability that a second domain will be in proximity to its target sequence when it undergoes transient denaturation.

It is also relevant to point out that many regions of chromosomal DNA exist in a supercoiled state. Since supercoiling promotes DNA breathing, the methods and compositions of the present invention will be useful in the targeting and modification of genes in living cells, in applications such as gene therapy. For instance, the unrestrained superhelical state of transcriptionally active genes can render them particularly susceptible to targeting and modification by the practice of the invention.

First Domain

The first domain can function to increase the local concentration of the oligonucleotide of the invention in the vicinity of the target sequence, through molecular interactions with a site adjacent to the target sequence. The first domain can comprise any molecular entity capable of sequence-specific recognition of double-stranded DNA. Such sequence-specific recognition can be mediated by electrostatic interactions, hydrophobic interactions, or any other type of covalent or non-covalent chemical interaction. Examples of moieties which can comprise part of a first functional domain include, but are not limited to, minor groove binding agents, antibiotics, intercalating agents, peptides, polypeptides and oligonucleotides.

Minor groove binding agents include substances which, by virtue of their steric and/or electrostatic properties, interact preferentially with the minor groove of double-stranded DNA. Certain of these exhibit a preference for particular sequence compositions. For instance, certain minor groove binders, such as netropsin, distamycin and CC 1065 (an antibiotic containing three repeating 1,2-dihydro-3H-pyrrolo[3,2-e] indole subunits wherein the third subunit is conjugated to a cyclopropapyrroloindole moiety) bind specifically in the minor groove of AT-rich sequences, particularly runs of A or T. WO 96/32496.

Many antibiotics are known to exert their effects by binding to DNA. Binding of antibiotics to DNA is often sequence-specific or exhibits sequence preferences, as discussed above. Actinomycin, for instance, is a relatively GC-specific DNA binding agent.

Certain peptide and polypeptide sequences bind to double-stranded DNA in a sequence-specific manner. For example, transcription factors assist in aligning RNA polymerase at the transcriptional startsite of a gene through sequence-specific interaction with DNA in the promoter or enhancer regions of the gene. Defined regions within the polypeptide sequence of various transcription factors have been shown to be responsible for sequence-specific binding to DNA. These regions include, but are not limited to, motifs known as the leucine zipper, the helix-loop-helix (HLH) domain, the zinc finger, the bZIP domain, the homeobox, and others. The amino acid sequence of these motifs are known and, in some cases, amino acids that are critical for sequence specificity have been identified. Such peptide sequences can be obtained through recombinant DNA cloning and expression techniques or by chemical synthesis, and can be attached to an oligonucleotide by methods known in the art. See, for example, Reed et al. (1995) *Bioconjugate Chem.* 6:101–108.

In a preferred embodiment, the first domain will comprise a "triplex guide sequence," i.e., a nucleotide sequence capable of forming a base-paired triplex with a site adjacent to the target sequence. Triplex formation refers to the ability of a single-stranded oligonucleotide to bind to a double-stranded oligonucleotide to form a stable three-stranded structure in which each of the three strands interacts with one or more other strands by hydrogen bonding between the heterocyclic bases. The hydrogen bonding between the single-stranded oligonucleotide and one of the strands of the duplex can, for example, be mediated by Hoogsteen base-pairing, reverse Hoogsteen base-pairing or an equivalent type of base-pairing. In the C,T triplex motif, an oligonucleotide containing $N^3$-protonated C residues ($C^+$) and/or T residues is able to form a triplex with a polypurine stretch, in which the third strand is aligned parallel to the polypurine-containing strand and the triplex is stabilized by Hoogsteen base-pairing between $C^+$ and G and between T and A. In the G,A triplex motif, an oligonucleotide containing G residues and/or A residues is able to form a triplex with a polypurine stretch, in which the third strand is aligned antiparallel to the polypurine-containing strand and the triplex is stabilized by reverse Hoogsteen base-pairing between G and G and between A and A. In the G,T triplex motif, an oligonucleotide containing G residues and/or T residues is able to form a triplex with a polypurine stretch, in which the third strand may be aligned either parallel or antiparallel to the polypurine-containing strand and the triplex may be stabilized by either Hoogsteen or reverse Hoogsteen base-pairing between G and G and between T and A.

Modified bases and base analogues, able to form Hoogsteen and reverse Hoogsteen base pairs with the naturally-occurring bases, are known in the art. Examples include, but are not limited to, 8-oxo-adenosine, pseudoisocytidine, 5-methyl cytidine, inosine, 2-aminopurine and various pyrrolo- and pyrazolopyrimidine derivatives. Similarly, modified sugar residues or analogues, for example 2'-O-methylribose or peptide nucleic acid backbones, can also form part of a third strand. See, for example, Sun and Hélène (1993) *Curr. Opin. Struct. Biol.* 3:345–356. Non-nucleotide macromolecules capable of triplex formation or capable of any type of sequence-specific interaction with a double-stranded DNA molecule are useful in the methods and compositions of the invention. Examples include, but are not limited to, peptide nucleic acids, minor groove-binding agents and antibiotics. New modified bases, base analogues, modified sugars, sugar analogues, modified phosphates and phosphate analogues capable of participating in triplex formation can be developed by methods known in the art, and will be useful in the methods and compositions of the invention.

In a preferred embodiment, the triplex guide sequence is less than about 30 nucleotides in length, more preferably, less than about 20 nucleotides, and, most preferably, between about 6 to about 15 nucleotides in length. The triplex guide sequence is designed to form a triplex with a homopurine/homopyrimidine run in a double-stranded polynucleotide by forming Hoogsteen, reverse Hoogsteen or equivalent base pairs with the strand containing the homopurine run. One or more pyrimidine interruptions in the homopurine run can be tolerated, and still allow triplex formation to occur. See, for example, Zhou et al. (1995) *J. Am. Chem. Soc.* 117:10425–10428. New modified bases, base analogues, modified sugars, sugar analogues, modified phosphates and phosphate analogues capable of facilitating triplex formation, by any mechanism whatsoever, with sequences containing one or more pyrimidine interruptions, can be developed by methods known in the art, and will be useful in the methods and compositions of the invention.

It is not required, for the practice of the invention, that the interaction between the first domain of the oligonucleotide and the target sequence confer absolute sequence specificity. Indeed, it can often be the case that the first domain will direct the oligonucleotide of which it is a part to several sites on a genome or a DNA molecule. In these cases, the sequence of the second domain (which is complementary, in the Watson-Crick sense, with the target sequence) will determine which of those several sites is chosen for targeting or modification and, hence, will determine the ultimate specificity of the interaction. However, in these cases the first domain serves the important purpose of tethering the oligonucleotide to a subset of sites on the DNA molecule of interest, thereby concentrating the oligonucleotide at a limited number of potential target sites.

In a preferred embodiment, wherein the first functional domain comprises a nucleotide sequence designed to form a triplex with a sequence in the vicinity of the target sequence, additional moieties can be added to the first functional domain to facilitate triplex formation. For instance, triplex formation at homopurine runs in duplex DNA is enhanced by minor groove binders. Robles et al. (1996) *J. Am. Chem. Soc.* 118:5820–5821 and Szewczyk et al. (1996) *J. Am. Chem. Soc.* 118:6778–6779. A preferred triplex stabilizer is coralyne. Lee et al. (1993) *Biochemistry* 32:5591–5597. Other triplex stabilizers include benzo[a]pyridoquinoxalines (Marchand el al. (1996) *Biochemistry* 35:5022–5032), naphthylquinolines (Wilson et al. (1993) *Biochemistry* 32:10614–10621), and related molecules. Intercalating agents which stabilize triplex structures [Escudé et al. (1995) *J. Am. Chem. Soc.* 117:10212–10219] are also useful in the methods of the invention.

Triplex-stabilizing agents can be attached to the first functional domain by any method known in the art. See, for example, Mouscadet et al. (1994) *Biochemistry* 33:4187–4196. Furthermore, various modified bases are known in the art and/or can be developed by one skilled in the art, that are capable of participating in and/or strengthening, Hoogsteen, reverse Hoogsteen or equivalent base-pairing. See, for example, Sun et al. (1993) *Curr. Opin. Struct. Biol.* 3:345–356. Such modified bases are also useful in the practice of the present invention.

Second Domain

The second domain is designed to be substantially complementary, in the Watson-Crick sense, to a target sequence in a double-stranded polynucleotide. It is brought into proximity to its complementary target sequence by virtue of the first functional domain of the oligonucleotide or oligonucleotide composition, as described above. The second functional domain binds, by Watson-Crick base-pairing, to the target sequence and, in so binding, either targets or modifies the target sequence. Modification can be direct or indirect. Absolute, 100% complementarity between the second functional domain and the target sequence is not required. A degree of complementarity sufficient to provide for stable duplex formation between the second functional domain and the target sequence under the particular conditions of the interaction (i.e., substantial complementarity) is all that is required. In the case wherein the second domain comprises an attached modifying group, the oligonucleotide-target duplex need only be stable enough for the modifying agent to exert its effect. Consequently, approximately 50% complementarity, more preferably 60%, even more preferably 75%, still more preferably 90% and most preferably, greater than 90% homology between the second functional domain and the target sequence is preferred in the practice of the invention. The length of the second domain will range from about 6 to about 50 nucleotides, more preferably from about 8 to about 30 nucleotides, and most preferably from about 10 to about 20 nucleotides.

Base-pairing between the second domain and the target sequence may be energetically unfavorable. This is because the target sequence is usually part of a long base-paired duplex having greater thermodynamic stability than the D-loop structure that would be formed by base-pairing between the second domain and its target sequence. Thus, to "lock-in" the interaction between the second domain and the target sequence, the second domain may optionally carry a modifying group or crosslinking agent. Crosslinking agents useful in the practice of the invention are capable of forming a covalent bond between the second domain and the target sequence. Alternatively, a modifying group, attached to the second domain, may react with the target sequence such that, even if the complex between the second domain and the target sequence dissociates, the target sequence remains modified.

Complementary base-pairing between the second functional domain and the target sequence can be enhanced by several means. For instance, certain modified nucleotides or nucleotide analogues can be used which, when incorporated into the sequence of the oligonucleotides of the invention, strengthen Watson-Crick base-pairing. In some cases, this will give the oligonucleotides of the invention the properties of selective binding complementary oligonucleotides, as described in PCT/US96/15934. In addition, it is possible to attach to the second functional domain non-nucleotide moieties which increase the rate and/or the degree of base pair formation. These include, but are not limited to, intercalating agents [Letsinger & Schott (1981) *J. Am. Chem. Soc.* 103:7394–7396; Asseline et al. (1984) *Proc. Natl. Acad. Sci. USA* 81:3297–3301; Benimetskaya et al. (1989) *Biopolymers* 28:1129–1147; and Lokhov et al. (1992) *Bioconjugate Chem.*, 3:414–419] and minor groove binders [WO 96/32496; Sinyakov et al. (1995) *J. Am. Chem. Soc.* 117:4995–4996 and Lukhtanov et al. (1995) *Bioconjugate Chem.* 6:418–426]. Unconjugated (i.e., not attached to the second functional domain) duplex-stabilizing moieties which favor base-pairing between the second functional domain and the target sequence, such as intercalating agents, can also be present. Strengthening of the base-pairing interaction between the second domain of the oligonucleotide and its target sequence can endow the newly-formed oligonucleotide-DNA hybrid with greater stability than the original DNA-DNA duplex. In this case, the efficiency of modification would be correspondingly high.

Alternatively, the length and/or base composition of the second functional domain can be designed to ensure that a specific stable duplex is formed between the second functional domain and the target nucleotide sequence under the conditions of their interaction. The dependence of duplex stability on innate factors such as base composition and duplex length, and on environmental conditions such as temperature, ionic strength, and solvent concentration, is well-known in the art and can be easily determined by one of skill in the art. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, el al., CURRENT PROTOCOLS IN MOLECULAR BIOLOGY, John Wiley & Sons (1987, 1988, 1989, 1990, 1991, 1992, 1993, 1994, 1995, 1996); Hames & Higgins (eds.), NUCLEIC ACID HYBRIDIZATION: A PRACTICAL APPROACH, IRL Press (1985), and related works. Accordingly, the length of the second domain will range from about 6 to about 50 nucleotides, more preferably from about 8 to about 30 nucleotides, and most preferably from about 10 to about 20 nucleotides.

Attachment of first domain to second domain

In the oligonucleotides of the present invention, the first domain can be linked to the second domain by any method known in the art. For example, an oligonucleotide corresponding to the nucleotide sequence of the second functional domain can be synthesized with a reactive group at its 5' or 3' terminus. A first domain moiety, such as a peptide or amino acid sequence can then be attached to the reactive group by methods known to one of skill in the art. See, for example, Reed et al. (1995) *Bioconjugate Chem.* 6:101–108; Corey et al. (1995) *Bioconjug. Chem.* 6:93–100; and Iyer et al. (1995) *J. Biol. Chem.* 270:14712–14717. Examples of reactive groups include amino groups, thio groups, and groups with similar properties. These groups can be attached to oligonucleotides by automated synthesis using precursors containing these functional groups, in protected form, which are commercially available from Glen Research, Sterling, Va.; Applied Biosystems, Foster City, Calif.; and Clontech, Palo Alto, Calif., for example. Following synthesis, the reactive group is deprotected along with the functional groups of the bases and the internucleotide phosphate groups, by methods known in the art. See, for example, Gait (ed.), OLIGONUCLEOTIDES SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

Minor groove binders, antibiotics, intercalators, and peptides can be attached to oligonucleotides by methods known in the art. See, for example, U.S. Pat. No. 4,835,263; WO 94/13325; WO 96/32496; Lukhtanov et al. (1996) *Nucleic Acids Res.* 24:683–687; Lukhtanov et al. (1995) *Bioconjugate Chemistry* 6:418–426; Kutyavin et al. (1995) *J. Am. Chem. Soc.* 117:4995–4996; and Reed et al. (1995) *Bioconjugate Chemistry* 6:101–108.

In a preferred embodiment of the invention, the first functional domain is an oligonucleotide sequence that forms a triplex with a sequence adjacent to the target sequence. In this case, the sequences of the first and second functional domains can be synthesized as a single oligonucleotide.

It should also be apparent that, although the first and second domains will most often be directly contiguous to each other in the compositions of the invention, direct contiguity is not required. Indeed, there can be "filler sequence" between the first and second domains comprising nucleotides, amino acids or other chemical linkers as are known in the art.

Modifying groups

Once a D-loop is formed by an oligonucleotide of the invention, one or more optional modifying groups present on the second segment can serve to covalently link the oligonucleotide to the target sequence, or to react with one or more nucleotides in the target sequence to generate a mutation, a pre-mutagenic lesion or some other type of modification of the target sequence. Covalent linkage of the oligonucleotide of the invention to the target sequence, for example, is likely to block the regulatory or coding function of the target sequence, resulting in functional mutation of the target sequence.

Modification of the target sequence can also be achieved directly by the binding of the second functional domain to the target sequence. Direct modification can ensue, for example, if base-pairing between the second functional domain and the target sequence blocks some function of the target sequence, such as protein binding, binding of another nucleic acid, or coding capacity. The ability of the oligonucleotides of the invention to achieve direct modification can be enhanced by the attachment of reactive groups that are able to form covalent bonds between the oligonucleotide and the target sequence, thereby crosslinking the oligonucleotide to the target sequence. Non-limiting examples of such reactive groups include electrophilic groups, haloacyl groups, haloalkyl groups, nitrogen mustards, bifunctional nitrogen mustards, sulfonyl halides, sulfonium salts, photoactivatible crosslinking agents such as psoralen and related compounds, and moieties containing an electrophilic cyclopropyl group, such as cyclopropapyrroloindole and its analogues. WO 96/32496; Lukhtanov et al. (1996) *Nucleic Acid Res.* 24:683–687.

Thus, in one aspect of the invention, a modifying group, such as a chemically reactive group, can optionally be part of the second functional domain. The modifying group can participate in direct modification of the target sequence by crosslinking the oligonucleotide of the invention to the target sequence, or it can facilitate indirect modification of the target sequence. Indirect modification can result, for instance, from the reaction of the modifying group with a specific functional group of a nucleotide in the target sequence, to generate a pre-mutagenic lesion in the target sequence. This pre-mutagenic lesion can be converted, by normal cellular processes of replication, recombination and/ or repair, to a heritable change in the nucleotide sequence of the target, such as a base change, insertion, deletion or transposition. The oligonucleotides of the invention are therefore capable of acting as site-specific mutagens. Thus, in one aspect, the invention provides a method for site-specific mutagenesis of a double-stranded nucleic acid.

A modifying group can be any chemical moiety capable of interacting with a functional group in the target sequence. In one aspect of the invention, the modifying group can be an electrophilic group which is part of a cross-linking agent. In the simplest terms the cross-linking agent comprises three groups or moieties, namely the reactive group E (which is typically and preferably an electrophilic group such as an electrophilic carbon), that carries a leaving group (L), and an "arm" (A), the electrophilic group E being attached to or being part of the arm A, which attaches the electrophilic group to the oligonucleotide. The leaving group L and/or leaving group-electrophilic group combination E—L can be chosen from, for example, such groups as chloro, bromo, iodo, $SO_2R'''$, or $S^+R'''R''''$, where each of R''' and R'''' is independently $C_{1-6}$ alkyl or aryl or R''' and R'''' together form a $C_{1-6}$ alkylene bridge. Chloro, bromo and iodo are preferred. Within these groups haloacetyl groups such as —$COCH_2I$, and bifunctional "nitrogen mustards", such as —N—$[(CH_2)_2—Cl]_2$ are preferred.

Attachment of the modifying group to the second domain can be at any site within the second domain, using methods that are well-known to those of skill in the art. See, for example, WO 96/40711. Examples of sites at which a modifying group can be attached include, but are not limited to, the 5' end of the second domain, the 3' end of the second domain, an internal region of the second domain, a base or modified base residue, a base analogue, a sugar or modified sugar residue, and a phosphate or modified phosphate residue. Base analogues which can be included in the compositions of the invention include, but are not limited to, pyrazolopyrimidines, such as those described in WO 90/03370 and in co-owned U.S. patent application Ser. No. 08/848,373, filed Apr. 30, 1997. A preferred site of attachment is the C3 position of a pyrazolopyrimidine.

Synthesis of oligonucleotides

Oligonucleotides can be chemically synthesized by automated methods that are well-known in the art. See, for example, U.S. Pat. No. 5,419,966; Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991). Oligonucleotides can be synthesized using standard commercial phosphoramidite chemistry, H-phosphonate chemistry, or any other type of chemistry known in the art.

Methods are available in the art for the synthesis of oligonucleotides containing the naturally-occurring nucleotide subunits, as well as a wide variety of modified nucleotides, including base analogues, modified sugars and sugar analogues, and modified phosphate linkages. The naturally-occurring heterocyclic bases commonly found in nucleic acids (uracil, thymine, cytosine, adenine and guanine), as well as naturally-occurring and synthetic modified bases and base analogues are useful in the practice of the invention. Such naturally-occurring and synthetic modified bases and base analogues can include, but are not limited to, hypoxanthine, 2-aminoadenine, 2-thiouracil, 2-thiothymine, 5-$N^4$ ethenocytosine, 4-aminopyrazolo[3,4-d]pyrimidine, and 6-amino-4-hydroxy-pyrazolo[3,4-d]pyrimidine. Kutyavin el al (1996) *Biochemistry* 34:11170–11176; Webb and Matteucci (1986) *Nucleic Acids Res.* 14:7661–7674; Webb and Matteucci (1986) *J. Am. Chem. Soc.* 108:2764; and Kazimierczuk el al. (1984) *J. Am. Chem. Soc.* 106:6379–6382.

The glycoside portion of the nucleotide subunits of the oligonucleotides and oligonucleotide compositions of the invention will comprise, in a preferred embodiment, 2-deoxyribofuranose. Other sugars (such as D-ribofuranose and D-glucose), sugar analogues and modified sugars, as are known in the art (such as 2-fluororibose, 2-O alkylribofuranose and 2-O alkenylribofuranose, wherein the alkyl group comprises 1 to 5 carbon atoms and the alkenyl group comprises 2 to 5 carbon atoms) are also useful in the compositions of the invention.

The oligonucleotides and oligonucleotide compositions of the invention are comprised of nucleotide subunits joined by internucleotide linkages. Often the internucleotide linkage takes the form of a phosphate backbone. The backbone may comprise phosphodiester linkages, as are commonly found in naturally-occurring nucleic acids, or various "modified" linkages, such as phosphorothioates and methylphosphonates, to name a but a few. The recently-described 3'-amino-2',3'-dideoxynucleoside 3'-N-5'-P phosphoramidate backbone is also useful in the compositions of the invention. Gryaznov et al. (1994) *J. Am. Chem. Soc.* 116:3143–3144. Other modified backbones, as are known in the art, are also useful in the practice of the invention, for example, U.S. Pat. No. 5,602,240; and Gryaznov et al. (1992) *Nucleic Acids Res.* 20:3403–3409.

It will be clear to one of skill in the art that the primary structural limitations of the various component bases, sugars and internucleotide linkages of the invention are related to the ability of the domains of the oligonucleotide to participate in either triplex formation or Watson-Crick-type base-pairing. Accordingly, a large number of structural variations, some of which have been described, are possible.

Uses for the oligonucleotides of the invention: methods for modification of a target sequence in double-stranded DNA The methods described in the present application can be performed in vitro, for example to modify isolated, purified DNA or to modify the genome of a cultured cell. In addition, the methods of the invention can be practiced in vivo, by administration of a modified oligonucleotide of the invention to a living subject.

The oligonucleotides and oligonucleotide compositions of the invention are administered to cells by any method of nucleic acid transfer known in the art, including, but not limited to, transformation, co-precipitation, electroporation, neutral or cationic liposome-mediated transfer, microinjection or gene gun. The oligonucleotides and oligonucleotide compositions can be covalently attached to carriers and/or connected to carriers by cleavable linkers, such carriers and linkers including, but not limited to, those disclosed in co-owned U.S. Pat. No. 5,574,142. The oligonucleotides and oligonucleotide compositions of the invention are suitable for in vitro, in vivo and ex vivo therapy and can be administered parenterally, intravenously, subcutaneously, orally or by any other method known in the art.

The target sequence can reside in a chromosomal gene of a subject plant or animal, or in the genome of a virus, bacteria, fungus or other pathogen which can be present in the cells of a subject.

The oligonucleotides and oligonucleotide compositions of the invention can be used to induce mutation in a deleterious gene (for example an oncogene or an essential gene of a pathogen) or to correct a mutation in a beneficial gene (such as, for example, a tumor suppressor gene).

Mutation can occur in one of several ways: by a change in nucleotide sequence, by insertion, by deletion or by transposition. Certain mutations can result in a change of function of the mutated gene. Some examples of mutations which alter gene function include, but are not limited to, insertion or deletion of one or more nucleotides leading to a change in the reading frame of the encoded protein, conversion of a coding sequence to a translational stop codon, a change in a mRNA splicing signal, changes in promoter or enhancer sequences affecting transcriptional initiation, changes to 5' untranslated sequences that reduce or abolish translational initiation, sequence changes within the coding region that reduce the rate of transcriptional elongation, and alterations in the 3' untranslated region leading to altered mRNA stability. It should be appreciated that, in certain cases, the method of the invention is also useful in correcting a defect in a gene, thereby restoring its activity or altering its activity to resemble more closely that of the corresponding normal gene.

Also of use in the present invention are oligonucleotides that are capable of either triplex formation with a double-stranded nucleic acid target or duplex formation with a complementary strand (by Watson-Crick base-pairing), but which do not necessarily comprise traditional nucleoside or nucleotide subunits, for example, peptide nucleic acids [Nielsen et al. (1991) *Science* 254: 1497–1500; and Demidov et al. (1995) *Proc. Natl. Acad. Sci. USA* 92:2637–2641] or bicyclo DNA oligomers [Bolli et al. (1996) *Nucleic acids Res.* 24: 4660–4667] or related structures.

EXAMPLES

Example 1
Preferential Interaction of Oligonucleotides Containing a Triplex-forming Domain and a D-loop-forming Domain with Supercoiled DNA A schematic of the experiment is presented in FIG. 1A. The target sequence (SEQ ID NOs: 1 and 2), in plasmid pHG1, contains a 20-base homopurine stretch identified in FIG. 1B as the "triplex" region. The regions flanking the triplex region in pHG1 are labeled "D-loop" in FIG. 1B. The sequences of the oligonucleotides used in these experiments, and their relationship to the target sequence, are listed in FIG. 1B. Oligonucleotide 1 (SEQ ID NO:3) comprises a "triplex guide sequence" capable of forming a pyrimidine motif triplex with the triplex domain. Oligonucleotides 2 (SEQ ID NO:4) and 4 (SEQ ID NO:7) are complementary to the D-loop regions located to the 5'- and 3'- sides of the triplex guide sequence, respectively. Oligonucleotides 3 (SEQ ID NO:5) and 5 (SEQ ID NO:8) contain the triplex guide sequence and the D-loop-forming domains found in oligonucleotides 2 and 4, respectively. Oligonucleotides 7 (SEQ ID NO:6) and 8 (SEQ ID NO:9) are identical to oligonucleotides 3 (SEQ ID NO:5) and 5 (SEQ ID NO:8) but contain a reactive bromacetamido group attached to a deoxyuridine residue in the D-loop domain.

Because negative supercoiling reduces the kinetic and thermodynamic barriers to D-loop formation, linearized (form III), supercoiled (form I), and highly supercoiled (form $I^h$) preparations of pHG1 were prepared. As a control for sequence specificity, a highly supercoiled preparation (form $I^h$) of plasmid pGFIB1, which lacks the homopurine run, but contains the D-loop sequence, was used.

Figure 2:
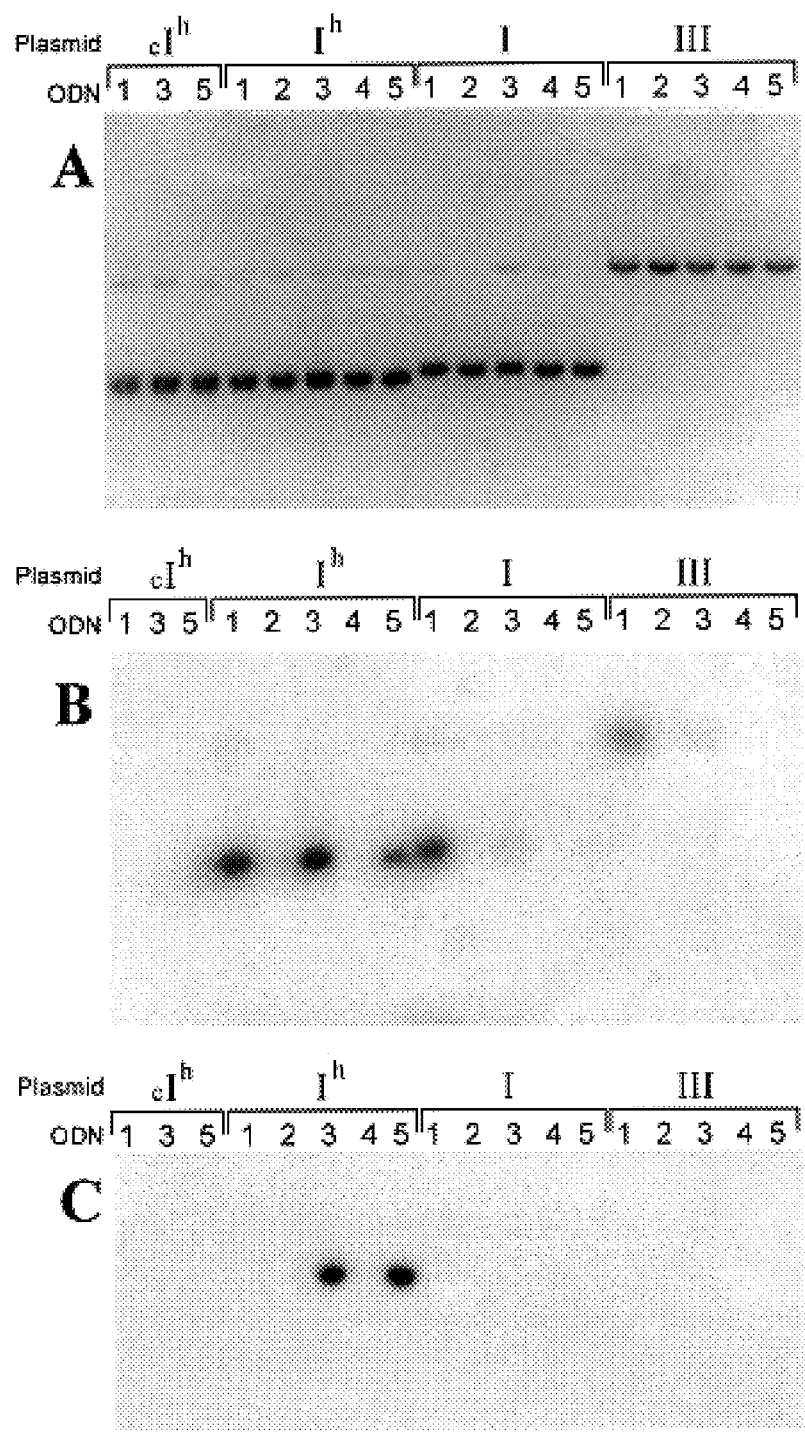
FIG. 2 shows photographs of 0.8% agarose gels used to detect triplex formation and D-loop formation.

Oligonucleotides were 5'-labeled with $\gamma$-$^{32}$P-ATP and polynucleotide kinase. Labeled oligonucleotides (3.6 nM) were incubated 42 hr at room temperature with 36 nM pGFIB1 (form $cI^1$) or pHG1 (forms $I^h$, I, and III) in 25 mM sodium cacodylate, pH 6.0, 10 mM MgCl$_2$. Aliquots of the reaction mixtures were analyzed for complex formation by electrophoresis in nondenaturing 0.8% agarose gels. Two buffer systems were used. The first, used to detect triple-stranded complexes, contained 90 mM Tris-OAc, pH 6.0, 1 mM Mg(OAc)$_2$ and was run for 14 hr at 20 V (FIG. 2B). The second buffer system, used for detection of D-loop complexes, contained 90 mM Tris-borate, pH 8.0, 2 mM EDTA, and was run for 1.5 hr at 100 V (FIG. 2C). Labeled oligonucleotide was detected by autoradiography of the dried gels (FIGS. 2B and 2C). Plasmid DNA was visualized by staining a separate gel with ethidium bromide (FIG. 2A).

FIG. 2B shows that oligonucleotides 1 (SEQ ID NO:3), 3 (SEQ ID NO:5), and 5 (SEQ ID NO:8) formed stable triple strands with highly supercoiled, (form $I^h$) pHG1 but did not bind to highly supercoiled pGFIB1, which does not contain the triplex-forming region. As expected, triplex domain oligonucleotide 1 (SEQ ID NO:3) also formed a stable triplex with supercoiled (form I) and linearized (form III) pHG1, but D-loop domain oligonucleotides 2 (SEQ ID NO:4) and 4 (SEQ ID NO:7) did not form complexes under any circumstances. The inability of oligonucleotides 3 (SEQ ID NO:5) and 5 (SEQ ID NO:8) to form a triplex with supercoiled or linearized pHG1 indicated that the D-loop domains of these oligonucleotides were not hybridized to the target and in their single-stranded state destabilized the triplex.

FIG. 2C shows detection of stable D-loop complexes under conditions in which triplexes are unstable. In this gel oligonucleotides 3 (SEQ ID NO:5) and 5 (SEQ ID NO:8) were bound to highly supercoiled pHG1 but not to highly supercoiled pGFIB 1, confirming the results obtained by triplex formation analysis shown in FIG. 2B. No other complexes were observed. Hence D-loop formation required both a highly supercoiled substrate and an oligonucleotide containing a triplex guide sequence. Thus, oligonucleotides containing both a triplex-forming domain and a D-loop forming domain interact with highly supercoiled pHG1 by both Hoogsteen and Watson-Crick base pairing.

Example 2
Modification of Supercoiled DNA by Oligonucleotides Containing a Triplex-forming Domain and a D-loop-forming Domain with an Attached Modifying Agent Since D-loops are likely to exist transiently under physiological conditions, a reactive bromoacetamidopropyl group was attached to the D-loop domain in oligonucleotides 7 (SEQ ID NO:6) and 8 (SEQ ID NO:9) to capture this species. This group, attached to a deoxyuridine residue within the sequence 5'-UGC, is targeted to alkylate the guanine residue in the complementary 5'-GCA sequence, which will lead to strand scission following treatment with hot piperidine (see arrows in FIG. 1B). The ability of oligonucleotides 7 (SEQ ID NO:6) and 8 (SEQ ID NO:9) to alkylate a specific target sequence in pHG1 was determined by digestion of pHG1 with Pvu II following incubation with the oligonucleotides and analysis of the digestion products on denaturing polyacrylamide gels (FIG. 3).

Pvu II restriction occurs to the 5'side of nucleotides 53, 226, and 357 of the pHG1 plasmid to generate fragments of 131, 173, and 3,632 base pairs, as shown in FIG. 3A. Treatment with hot piperidine will induce strand breaks at the site of an alkylated A or G residue. The site on pHG1 targeted by oligonucleotide 7 (SEQ ID NO:6) occurs at guanine residue 193 of the pyrimidine-rich strand. If alkylation of this targeted residue occurs, the 173-nucleotide Pvu II fragment encompassing this site will be converted into fragments of 140 and 33 nucleotides by hot piperidine treatment Oligonucleotide 8 (SEQ ID NO:9) targets a G residue at nucleotide 228 of pHG1. This target site is too close to a Pvu II cleavage site (at nucleotide 226) for targeted alkylation to be detected by piperidine cleavage. However, binding of oligonucleotide 8 (SEQ ID NO:9) to its target site would be expected to block Pvu II cleavage of the site at nucleotide 226, resulting in the loss of the 173- and 131-nucleotide Pvu II cleavage products, and the appearance of a new 304-nucleotide fragment after Pvu II digestion.

Oligonucleotides 7 (SEQ ID NO:6) and 8 (SEQ ID NO:9), each at a concentration of 820 nM, were incubated with 3.85 nM pGFIB1 (form $cI^h$) or pGH1 (forms $I^h$, I, and III), to give a molar ratio of oligonucleotide to plasmid of 212:1, for 4 days at room temperature in 25 mM sodium cacodylate, pH 6.0, 10 mM MgCl$_2$. Reactions were diluted into 10 mM Tris, pH 8.0, 1 mM EDTA and processed through a Centricon® 30 membrane to remove excess oligonucleotide. The recovered plasmid was digested with Pvu II restriction endonuclease to generate three fragments 131, 173, and 3,632 base pairs in length and these fragments were dephosphorylated with calf intestinal alkaline phosphatase and end-labeled with γ-$^{32}$P-ATP and T4 polynucleotide kinase. Aliquots were electrophoresed in a 6% denaturing polyacrylamide gel either before (FIG. 3A) or after (FIG. 3B) treatment with hot piperidine (20 min at 90° C. followed by lyophilization).

Figure 3:
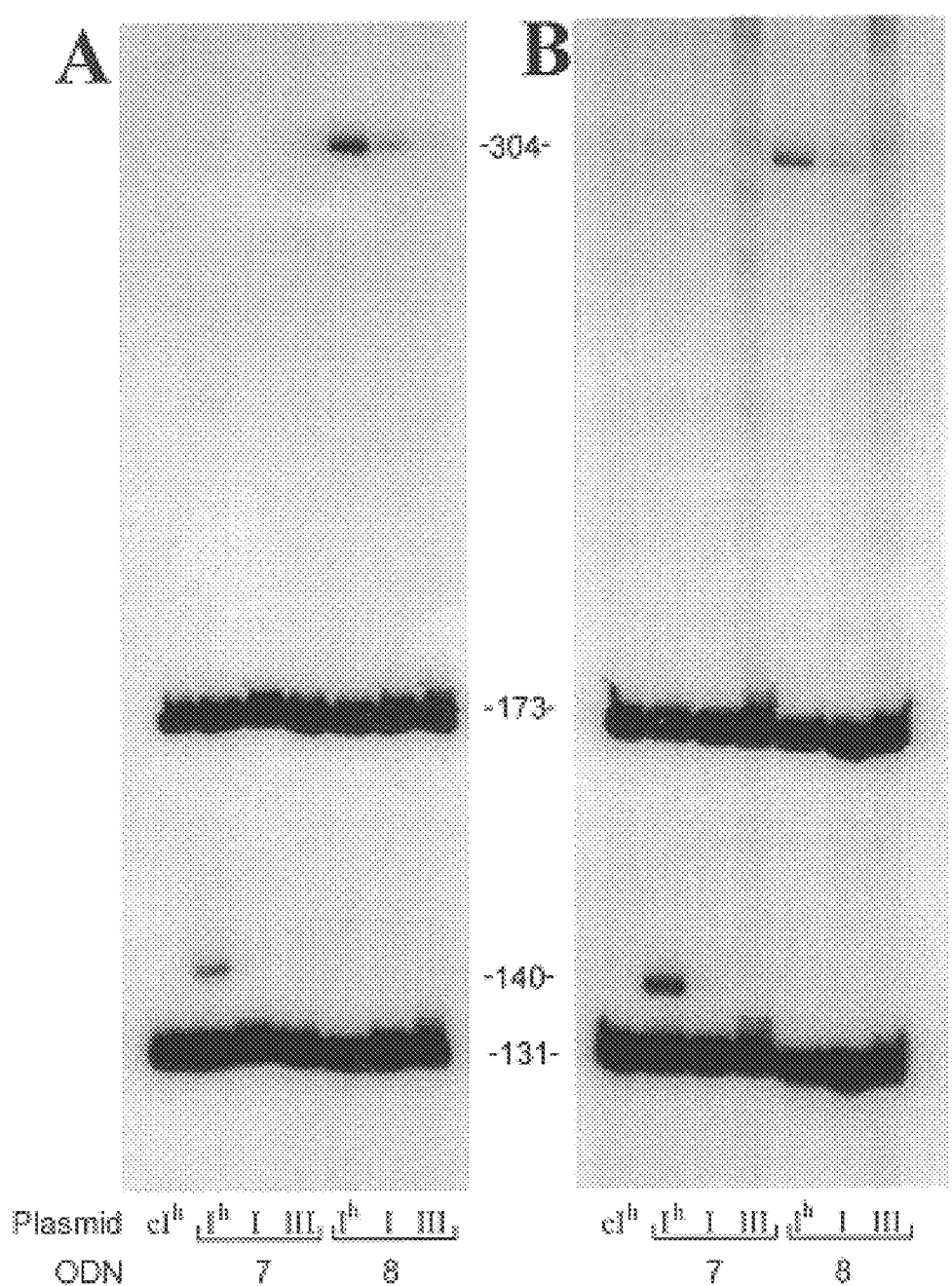
FIG. 3 demonstrates modification of a target sequence by an oligonucleotide. Electrophoresis on a denaturing 6% polyacrylamide gel is shown before (FIG. 3A) or after (FIG. 3B) treatment with hot piperidine. Detection is by autoradiography.

The results shown in FIG. 3 show that both oligonucleotides 7 (SEQ ID NO:6) and 8 (SEQ ID NO:9) alkylated their respective target guanine residue of highly supercoiled pHG1 with exceptional selectivity. Alkylation followed by strand scission at the target site for oligonucleotide 7 (SEQ ID NO:6) generated the expected 140-nucleotide fragment after hot piperidine treatment (FIG. 3B). The cleavage product generated by oligonucleotide 8 (SEQ ID NO:9), a fragment 175 bases in length, is obscured by a Pvu II restriction fragment of nearly the same length. However, the D-loop complex formed between highly supercoiled pHG1 and oligonucleotide 8 (SEQ ID NO:9) inhibited Pvu II digestion of its recognition site at nucleotide 226, generating a 304-nucleotide fragment. Piperidine treatment of the same samples (FIG. 3B) did not substantially change the electrophoretic pattern, indicating that most of the alkylated product had undergone cleavage during the 4-day incubation period. Reaction of oligonucleotides 7 and 8 was most pronounced with highly supercoiled pHG1 (form I$^h$); although reaction with supercoiled form I was also detectable (FIG. 3).

Example 3
Confirmation of D-loop-formation by Nuclease Sensitivity of the Displaced Strand Further evidence of D-loop formation was obtained by S1 nuclease treatment of complexes formed between oligonucleotide 3 or 5 and pHG1. Oligonucleotide (either oligonucleotide 3 or oligonucleotide 5) at a concentration of 3 μM was incubated with 30 nM target (pHG1; either form I or form I$^h$) for 42 hours at room temperature in 50 μl of 25 mM sodium cacodylate, pH 6.0, 10 mM MgCl$_2$. Then 2.5 Units of S1 nuclease was added and incubation was continued for 15 min. Reactions were terminated by addition of EDTA to a final concentration of 50 mM, followed by phenol/chloroform extraction and ethanol precipitation of the DNA. The S1 cleavage pattern was analyzed by primer extension, using the purine-containing strand of pHG1 as template. The primer had the following sequence:

5'-CCCTGGCGCCGCTTCTTTGAG-3' (SEQ ID NO:10)

and was complementary to a region of pHG1 that is 104 nucleotides upstream of the polypurine stretch used for triplex formation. Primer extension was conducted using the Sequenase® enzyme (Amersham Life Sciences) in the presence of [α-$^{35}$S] dATP. Runoff products were mapped relative to a sequencing ladder, using the same primer and template.

Figure 4:
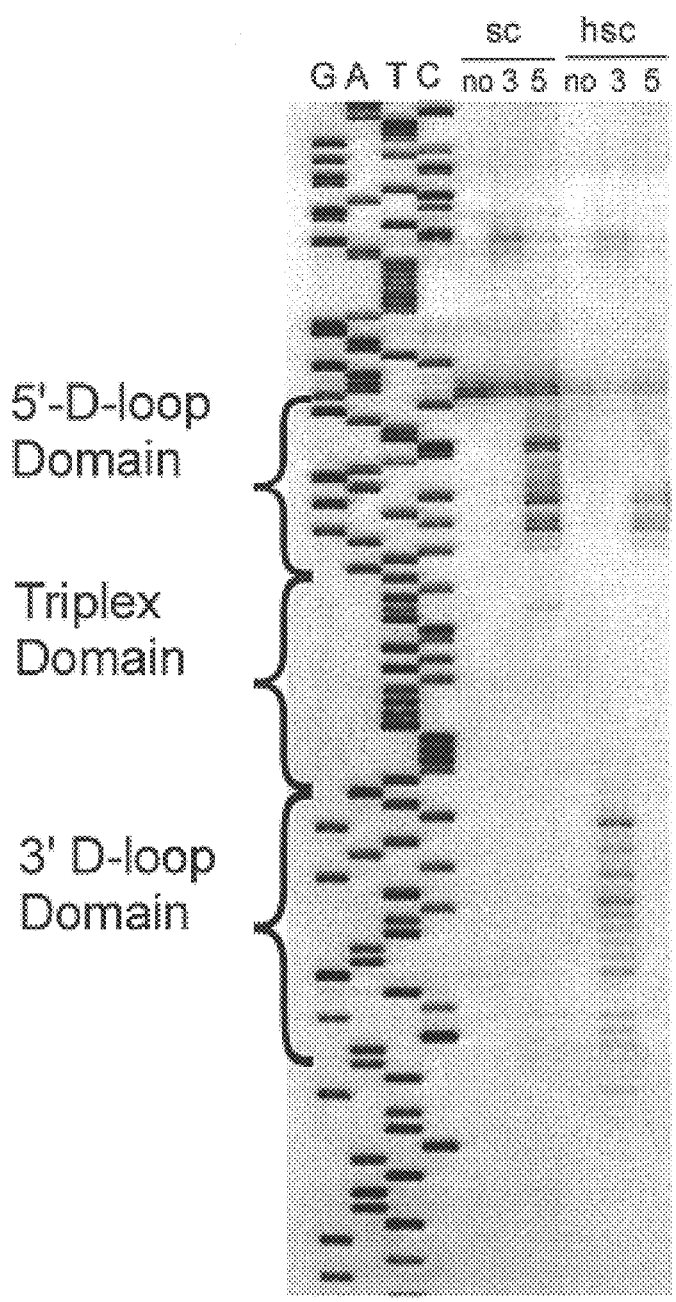
FIG. 4 shows an analysis of D-loop formation by S1 nuclease digestion of complexes formed between oligonucleotides and pHG1. Lanes labeled "G, A, T, C" comprise a sequencing ladder for alignment purposes. Lanes labeled "sc" refer to supercoiled (form I) pHG1 target, and lanes labeled "hsc" indicate that highly supercoiled (form I$^h$) pHG1 was used as target. Controls containing no oligonucleotide, or experiments containing oligonucleotide 3 or oligonucleotide 5 are indicated by "no," "3" and "5", respectively.

The results (FIG. 4) indicate that brief (15 min.) S1 nuclease treatment of complexes formed between oligonucleotide 3 or 5 and supercoiled or highly supercoiled pHG1 resulted in S1 cleavage in the D-loop region of the pHG1 strand having the same sequence as the D-loop-forming region of the oligonucleotide. This is indicative of the single-stranded character of this region of pHG1, since S1 is a single-strand-specific nuclease. The S1 assay also shows that oligonucleotide 5 forms a D-loop with the 5' D-loop domain of supercoiled (form I) pHG1, in agreement with the data from Example 2 showing crosslinking of oligonucleotide 8 to supercoiled pHG1. Finally, the lack of S1 cleavage of pHG1 in the absence of oligonucleotide (lanes labeled "no" in FIG. 4) indicates that both the supercoiled (form I) and highly supercoiled (form I$^h$) states of this plasmid ordinarily assume a double-stranded conformation in the D-loop-forming regions recognized by the oligonucleotides used here.

These results show that D-loop formation in B form DNA can be accomplished by the oligonucleotides and oligonucleotide compositions of the invention, which form sequence-specific complexes dependent upon both double-strand and single-strand sequence recognition. The reaction kinetics can be increased through the use of agents that facilitate triplex and duplex formation, as have been described herein.

Although the foregoing invention has been described in some detail by way of illustration and example for purposes of clarity of understanding, it will be apparent to those skilled in the art that certain changes and modifications may be practiced. Therefore the foregoing descriptions and examples should not be construed as limiting the scope of the invention.

What is claimed is:

1. A method for modifying a target nucleotide sequence in a double-stranded DNA molecule, said method comprising:
    contacting the double-stranded DNA molecule with an oligonucleotide composition comprising a first domain and a second domain;
    wherein the first domain serves to localize the oligonucleotide composition to the vicinity of the target nucleotide sequence;
    the second domain recognizes a single-stranded target nucleotide sequence; and wherein the second domain carries an attached modifying agent capable of modifying the target nucleotide sequence.

2. A method for modifying a target nucleotide sequence in a double-stranded DNA molecule, said method comprising:
    contacting the double-stranded DNA molecule with an oligonucleotide composition comprising a first domain and a second domain;
        wherein the first domain binds to a double-stranded DNA sequence in the vicinity of the target nucleotide sequence;
        the second domain is substantially complementary, in the Watson-Crick sense, to the target nucleotide sequence; and
        wherein the second domain carries an attached modifying agent capable of modifying the target nucleotide sequence.

3. The method according to claim 1 performed in vitro.

4. The method according to claim 1 performed in vivo.

5. The method according to claim 1 wherein the target nucleotide sequence is in a chromosomal gene of a plant or animal, a viral genome, a bacterial genome, or the genome of a pathogen.

6. The method according to claim 1 wherein the first domain comprises an intercalating agent.

7. The method according to claim 1 wherein the first domain comprises an antibiotic.

8. The method of claim 1 wherein the first domain comprises a minor groove binding agent.

9. The method according to claim 1 wherein the first domain comprises a sequence of amino acids.

10. The method according to claim 1 wherein the first domain comprises a peptide nucleic acid sequence.

11. The method according to claim 1 wherein the first domain comprises a sequence of nucleotides.

12. The method according to claim 11 wherein the first domain comprises an oligonucleotide sequence that binds to a site adjacent to or in the vicinity of the target sequence by triplex formation.

13. The method according to claim 12 wherein the first domain and the second domain base-pair with adjacent segments of the target nucleotide sequence.

14. The method according to claim 1 wherein the modifying agent is an electrophilic group.

15. The method according to claim 1 wherein the modifying agent is a photoactivatible cross-linking agent.

16. The method according to claim 14 wherein the modifying agent is located at the 5' end of the second domain.

17. The method according to claim 14 wherein the modifying agent is located at the 3' end of the second domain.

18. The method according to claim 14 wherein the modifying agent is selected from the group consisting of a nitrogen mustard, a bifunctional nitrogen mustard, a haloacyl group, a haloalkyl group, a sulfonyl halide, a sulfonium salt and a moiety containing an electrophilic cyclopropyl group.

19. The method according to claim 14 wherein the modifying agent is attached to a base residue.

20. The method according to claim 19 wherein the modifying agent is attached to a base analogue.

21. The method according to claim 20 wherein the modifying agent is attached to the C3 position of a pyrazolopyrimidine.

22. The method according to claim 12 further comprising the use of a triplex stabilizer.

23. The method according to claim 22 wherein the triplex stabilizer is coralyne.

24. The method according to claim 1 wherein modification of the target nucleotide sequence alters the activity of the double-stranded DNA molecule.

* * * * *